(12) United States Patent
Simhambhatla et al.

(10) Patent No.: US 6,270,522 B1
(45) Date of Patent: Aug. 7, 2001

(54) HIGH PRESSURE CATHETER BALLOON

(75) Inventors: Murthy V. Simhambhatla, San Jose; Venu Ghanta, Sunnyvale; Timoteo Tomas, Union City, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/469,728

(22) Filed: Dec. 21, 1999

(51) Int. Cl.$^7$ .................................................. A61F 2/06
(52) U.S. Cl. ......................................... 623/1.11; 606/194
(58) Field of Search .................................. 606/198, 194, 606/192; 623/1.11; 604/96.1, 103.06, 103.13, 103.11, 103.12

(56) References Cited

U.S. PATENT DOCUMENTS

| | | |
|---|---|---|
| 4,950,239 | 8/1990 | Gahara et al. ............... 604/96 |
| 5,304,340 | 4/1994 | Downey .................. 264/521 |
| 5,506,300 * | 4/1996 | Ward et al. ................ 525/88 |
| 5,587,125 * | 12/1996 | Roychowdhury ............ 604/96 |
| 5,797,877 | 8/1998 | Hamilton et al. ............ 604/96 |
| 5,830,182 | 11/1998 | Wang et al. ................ 604/96 |
| 5,908,406 | 6/1999 | Ostapchenko et al. ........ 604/96 |
| 6,004,339 * | 12/1999 | Wijay ..................... 606/192 |
| 6,013,728 * | 1/2000 | Chen et al. ................ 525/92 |
| 6,059,751 * | 5/2000 | Ostapchenko et al. ........ 604/96 |

FOREIGN PATENT DOCUMENTS 03023830 1/1991 (JP).

OTHER PUBLICATIONS

"Hytrel—polyester elastomer", DuPont Product and Properties Guide, pp. 1–10.
"Hytrel—polyester elastomer", DuPont Product Information, pp. 1–2.
Quirk et al., "Polyester Thermoplastics Elastomers", Handbook of Elastomers: New Developments and Technology, pp. 341–373.
Zaiser, "New Opportunities for Thermoplastic Elastomers", pp. 713–716.

* cited by examiner

*Primary Examiner*—Henry J. Recla
*Assistant Examiner*—(Jackie) Tan-Uyen T. Ho
(74) *Attorney, Agent, or Firm*—Heller Ehrman White & McAuliffe LLP

(57) ABSTRACT

A balloon formed of a single layer of polybutylene terephthalate and polytetramethylene ether glycol terephthalate copolymer in a substantially unblended form. The copolymer has a flexural modulus of greater than about 150,000 psi. The presently preferred copolymer is Hytrel® 8238 by DuPont. The balloon would be substantially unblended, defined as greater than about 60% by weight to about 100% by weight of the copolymer. The balloon is formed in a series of molds. The balloon exhibits high rupture pressure and low compliance coupled with good lesion cross and recross ability.

28 Claims, 1 Drawing Sheet

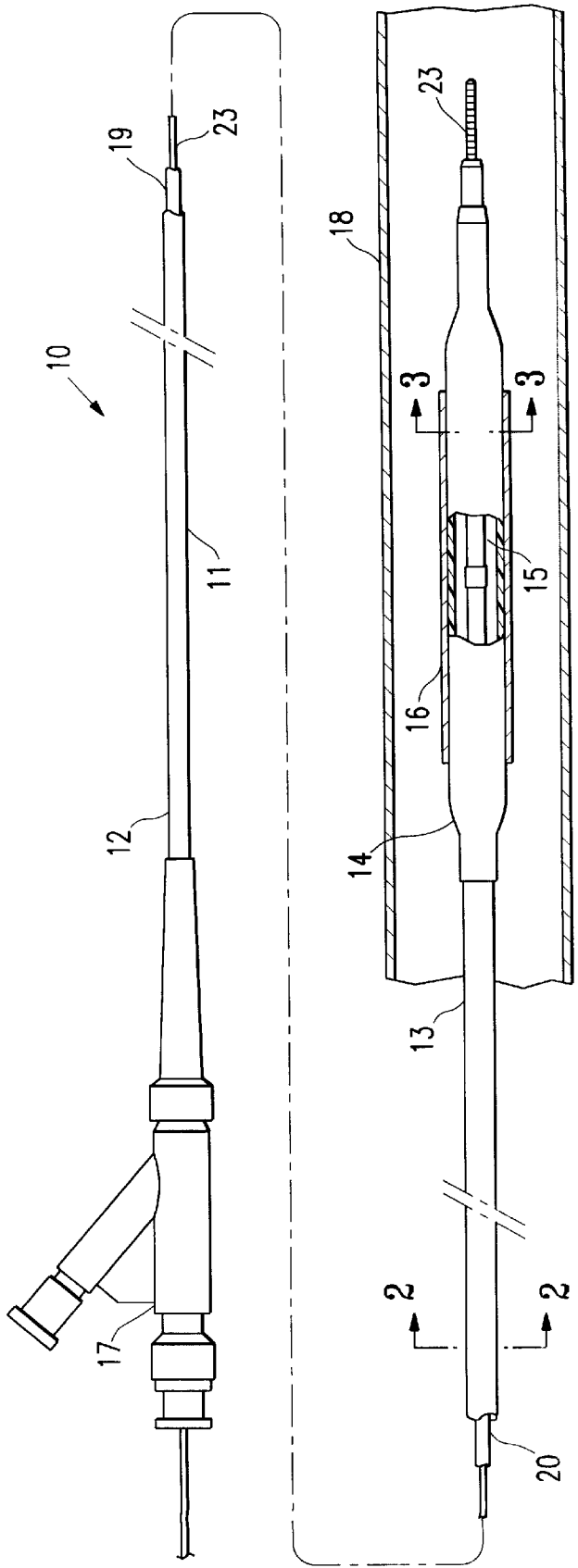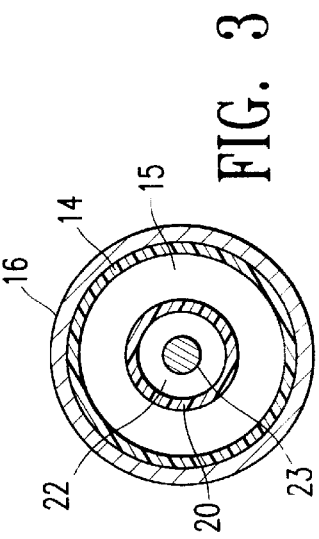

HIGH PRESSURE CATHETER BALLOON

BACKGROUND OF THE INVENTION

This invention generally relates to intravascular catheters, such as balloon dilatation catheters used in percutaneous transluminal coronary angioplasty (PTCA).

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow there through. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced until the preshaped distal tip of the guiding catheter is disposed within the aorta adjacent the ostium of the desired coronary artery, and the distal tip of the guiding catheter is then maneuvered into the ostium. A balloon dilatation catheter may then be advanced through the guiding catheter into the patient's coronary artery until the balloon on the catheter is disposed within the stenotic region of the patient's artery. The balloon is inflated to open up the arterial passageway and increase the blood flow through the artery. Generally, the inflated diameter of the balloon is approximately the same diameter as the native diameter of the body lumen being dilated so as to complete the dilatation but not over expand the artery wall. After the balloon is finally deflated, blood flow resumes through the dilated artery and the dilatation catheter can be removed therefrom.

To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

To properly position the balloon within the stenotic region, the balloon must be advancable within the patient's tortuous vasculature. Additionally, the balloon must be advanced across the stenosis, typically referred to as the ability to cross the stenosis. However, the design of balloon catheters must balance the competing concerns of flexibility and balloon softness required for trackability and crossability with balloon strength and low compliance required to expand against the stenosis.

Therefore, what has been needed is a balloon catheter with improved trackability, crossability and strength. The present invention satisfies these and other needs.

SUMMARY OF THE INVENTION

The invention is directed to a balloon formed of a single layer of a substantially unblended copolymer having a flexural modulus of at least 150 kpsi (1 GPa). A single layer is defined as one layer of copolymer used to manufacture the balloon. The copolymer is a copolymer of polybutylene terephthalate ("PBT") and polytetramethylene ether glycol terephthalate ("PTMEGT").

In a presently preferred embodiment, the copolymer is substantially unblended with any other material. Substantially unblended, for the purpose of this patent is defined as greater than about 60% by weight of the copolymer. In a more preferred embodiment, the balloon is formed of no less than about 95% by weight of the copolymer. The most preferred embodiment is about 100% by weight PBT and PTMEGT copolymer. Suitable polymeric materials for blending with the PBT and PTMEGT copolymer include polymers such as polyethylene terephthalate or polybutylene terephthalate to make a stiffer balloon.

A balloon catheter of the invention generally comprises a catheter having an elongated shaft with proximal and distal ends, an inflation lumen, and a single layered balloon formed of a copolymer made of polybutylene terephthalate and polytetramethylene ether glycol terephthalate. A suitable PBT and PTMEGT copolymer includes Hytrel® polymers from E.I. DuPont de Nemours and Company. Hytrel® is available in a range of grades. Properties of the grade are determined by the ratio of PTMEGT to PBT. The presently preferred copolymer is Hytrel® 8238, which has a shore durometer hardness of 82D.

In accordance with the invention, the balloon is formed of a polymeric material, whether 100% copolymer or substantially unblended, the polymeric material having a flexural modulus of greater than about 150 kpsi (1 GPa). The flexural modulus is a measure of the ratio of stress to strain during flexural deformation. Therefore, a high flexural modulus number means a material is harder to distort with increasing force. Preferably, the copolymer has a flexural modulus of at least 175 kpsi (1.17 GPa).

The material will have an elongation at break of at least about 200%, preferably about 350% or higher. The tensile strength of the material at break will be at least 5500 psi, preferably greater than about 6500 psi (45 MPa). The tensile strength for the most preferred material is about 7000 psi (48 MPa) or higher. The balloon made from the material will have an average rupture pressure of at least 18 atm, and is usually about 22 atm to about 26 atm for a balloon with a double wall thickness of about 0.0016 inches (0.04 millimeters).

The balloon of this invention will have a low compliance. The term complaint is understood to mean the measure of the increase in diameter of the balloon under pressure. Low compliance is meant to imply radial expansion less than about 0.045 millimeters per atmosphere of pressure applied (mm/atm). In the most preferred embodiment of the invention, the resulting balloon has a compliance of less than 0.02 mm/atm within the working range of the balloon of about 10 atm to about 18 atm.

Various designs for balloon catheters well known in the art may be used in the catheter of the invention. For example, the catheter may be a conventional over-the-wire dilatation catheter for angioplasty having a guidewire receiving lumen extending the length of the catheter shaft from a guidewire port in the proximal end of the shaft, or a rapid exchange dilatation catheter having a short guidewire lumen extending to the distal end of the shaft from a guidewire port located distal to the proximal end of the shaft. Additionally, the catheter may be used to deliver a stent mounted on the catheter balloon.

The balloon of the invention provides improved performance because of the strength of the material coupled with its unexpected tracking and crossing ability. The catheter of the invention has the unexpected ability to track as well as a catheter with a balloon formed of a more compliant material with a lower flexural modulus. Tracking is the ease that the balloon catheter moves through the blood vessel and advanced over the guidewire. Good tracking ability means the user feels less resistance. In addition, the balloon of this invention could cross a lesion which Nylon and Pellethane balloons known in the art could not cross. The balloon of this invention, once deflated, also had the ability to recross the lesion after initial dilation. Therefore, the balloon of this invention would make an excellent choice for physicians dealing with multiple stenosis and re-dilation cases.

The material properties of the balloon also make the invention ideal for stent implantation. The balloon has low compliance, coupled with high pressure capability. Therefore, the balloon of this invention would be used for a balloon catheter to cross a non-dilated lesion and expand to simultaneously dilate the lesion and implant the stent.

These and other advantages of the invention will become more apparent from the following detailed description of the invention and the accompanying exemplary drawings.

BRIEF DESCRIPTION OF THE DRAWINGS

FIG. 1 is an elevational view, partially in section, of a balloon catheter that embodies features of the invention, showing the balloon in an unexpanded state.

FIG. 2 is a transverse cross sectional view of the catheter of FIG. 1 taken along lines 2—2.

FIG. 3 is a transverse cross sectional view of the catheter of FIG. 1 taken along lines 3—3.

DETAILED DESCRIPTION OF THE INVENTION

As shown in FIGS. 1–3, the catheter 10 of the invention generally includes an elongated catheter shaft 11 having a proximal section 12 and distal section 13, an inflatable balloon 14 formed of substantially unblended PBT and PTMEGT copolymer on the distal section 13 of the catheter shaft 11, and an adapter 17 mounted on the proximal section 12 of shaft 11 to direct inflation fluid to the interior of the inflatable balloon. The embodiment shown in FIG. 1 includes a stent 16 disposed about the balloon 14. FIGS. 2 and 3 illustrate transverse cross sections of the catheter shown in FIG. 1, taken along lines 2—2 and 3—3 respectively.

In the embodiment illustrated in FIG. 1, the intravascular catheter 10 of the invention is an over-the-wire catheter, and is illustrated within a patient's body lumen 18 with the balloon 14 in an unexpanded state. The catheter shaft 11 has an outer tubular member 19 and an inner tubular member 20 disposed within the outer tubular member and defining, with the outer tubular member, annular inflation lumen 21. Inflation lumen 21 is in fluid communication with the interior chamber 15 of the inflatable balloon 14. The inner tubular member 20 has an inner lumen 22 extending therein, which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19.

The catheter 10 is advanced within the patient's vasculature. The balloon 14 on a distal section 13 is then positioned so that at least a length of the balloon is across a non-dilated region within the patient's vasculature. The balloon 14 is then expanded against the patient's lumen 18 to simutaneously dilate the undilated lesion and implant the stent 16.

The balloon 14 of the invention is formed of a single layer of PBT and PTMEGT copolymer. Preferably, the PBT and PTMEGT copolymer is a randomized block copolymer. Such presently preferred copolymers are Hytrel® copolymers provided by DuPont. Additionally, the preferred copolymer would have a hardness, Shore D scale of greater than about 72, preferably about 82. The copolymer is substantially unblended, defined earlier as having greater than about 60% by weight, preferably greater than about 95% of the PBT and PTMEGT copolymer.

The balloon 14 generally has a flexural modulus of greater than about 150 kpsi (1 GPa), preferably about 150 kpsi (1 GPa) to about 300 kpsi (2 GPa). Most preferably not less than about 175 kpsi (1.17 GPa). The compliance of the balloon 14 is less than 0.045 millimeters per atmosphere, and preferably less than 0.02 millimeters per atmosphere.

Balloon 14 has an average burst pressure of not less than about 270 psi to about 400 psi. Preferably, the average burst pressure is greater than about 330 psi. The wall hoop strength of balloon 14 is not less than about 20 kpsi, with a double wall thickness of at least 0.0007 inches (0.017 millimeters) to about 0.0025 inches (0.06 millimeters). Preferably, the double wall thickness is between 0.0015 (0.038 millimeters) and 0.0018 inches (0.046 millimeters) for a 3.0 millimeter diameter balloon.

The balloon is typically formed by extruding the polymer material to form a polymeric tube. The tube is placed in a balloon mold and exposed to elevated temperature and pressure to form the balloon. Both internal pressure and axial tension are applied to the polymer material. In a presently preferred embodiment, the balloon is formed by expanding the tube in two or more successively larger molds. The temperature may stay constant or be increased at each mold. Most preferably, the series will encompass at least three molds. Each successive mold will increase the radius of the mold. This process will prevent abrupt increases in wall hoop stress during balloon blowing.

Typically, the first mold increases the polymeric tube to about 30%–60% of the final diameter of the finished balloon. The second mold increases the polymeric tube to about 60%–90% of the final diameter of the finished balloon. The third mold has an inner diameter approximately equal to the outer diameter of the finished balloon. However, the number of molds, and the successive sizes are variable, based on the blend of copolymer used and the final diameter of the balloon.

EXAMPLE

A 3.0 mm balloon was made from 100% copolymer uses a three mold process. The balloon was 100% Hytrel 8238. The first mold expanded the tube to a 1.5 millimeter diameter. The mold exposed the tubing to a pressure of about 500 psi at a temperature of about 110° C. The second mold increased the diameter to 2.0 millimeters, but only employed a pressure of about 200 psi to about 400 psi at about 120° C. The final blow mold used a pressure of 500 psi to increase the balloon to its final diameter of 3.0 millimeters at about 130° C.

The resulting 3.0 millimeter balloon had compliance of 0.014 mm/atm. The double wall thickness was 0.0016 inches (0.04 millimeters). The balloon also had a wall hoop strength of 26.8 kpsi, and an average burst pressure of 383 psi.

Although individual features of embodiments of the invention may be shown in some of the drawings and not in others, those skilled in the art will recognize that individual features of one embodiment of the invention can be combined with any or all the features of another embodiment.

What is claimed is:

1. An inflatable single layered balloon for a medical device comprising a polymeric material, the polymeric material being a substantially unblended copolymer of polybutylene terephthalate and polytetramethylene ether glycol terephthalate, the copolymer having a flexural modulus of greater than about 150,000 psi.

2. The single layered balloon as in claim 1 wherein the copolymer is a randomized block copolymer.

3. The single layered balloon as in claim 1 wherein the copolymer has a hardness, shore D scale, of greater than about 72.

4. The single layered balloon as in claim 1 wherein the copolymer has a hardness, shore D scale, of about 72 to about 82.

5. The single layered balloon as in claim 1 wherein the copolymer has a hardness, shore D scale, of about 82.

6. The single layered balloon as in claim 1 wherein the balloon has greater than 60% by weight polybutylene terephthalate and polytetramethylene ether glycol terephthalate copolymer.

7. The single layered balloon as in claim 1 wherein the balloon has greater than 95% by weight polybutylene terephthalate and polytetramethylene ether glycol terephthalate copolymer.

8. The single layered balloon as in claim 1 wherein the copolymer has a flexural modulus of about 150,000 psi to about 300,000 psi.

9. The single layered balloon as in claim 1 wherein the copolymer has a flexural modulus of about 175,000 psi.

10. The single layered balloon as in claim 1 wherein the balloon has a compliance of less than about 0.045 millimeters per atmosphere within an inflation pressure range of 135 psi to 270 psi.

11. The single layered balloon as in claim 1 wherein the balloon has a compliance of less than about 0.02 millimeters per atmosphere within an inflation 0.10 pressure range of 135 psi to 270 psi.

12. The balloon as in claim 1 wherein the balloon has a wall strength of at least about 10,000 psi to about 30,000 psi.

13. The balloon as in claim 1 wherein the balloon has a wall strength of at least about 20,000 psi to about 30,000 psi.

14. The balloon as in claim 1 wherein the balloon has a wall strength of at least about 25,000 psi to about 30,000 psi.

15. The balloon as in claim 1 wherein the balloon has a double wall thickness of no greater than about 0.0025 inches.

16. The balloon as in claim 1 wherein the balloon has a double wall thickness of no greater than about 0.0015 inches.

17. The balloon as in claim 1 wherein the balloon has a double wall thickness of no greater than about 0.0009 inches.

18. The balloon as in claim 1 wherein the balloon has an average rupture pressure of at least about 270 psi.

19. The balloon as in claim 1 wherein the balloon has an average rupture pressure of at least about 345 psi.

20. The balloon as in claim 1 wherein the balloon has an outer diameter of about 1.5 millimeters to about 10 millimeters.

21. The balloon as in claim 1 wherein the balloon has an outer diameter of about 1.5 millimeters to about 5 millimeters.

22. An intraluminal balloon catheter, comprising:
   a) an elongated shaft having a proximal end, a distal end, an inflation lumen extending within at least a portion of a distal shaft section to a location spaced proximally from the distal end; and
   b) a single layered balloon for a medical device comprising a polymeric material, the polymeric material being a substantially unblended copolymer of polybutylene terephthalate and polytetramethylene ether glycol terephthalate, the copolymer having a flexural modulus of greater than about 150,000 psi.

23. The intraluminal catheter of claim 22 wherein the elongated shaft comprises an outer tubular member, and an inner tubular member having a lumen and being disposed within the outer tubular member and defining therewith the inflation lumen.

24. The intraluminal catheter of claim 22 further including a stent mounted on the balloon.

25. A method for implanting a stent within a patient, comprising
   a) advancing within the patient's vasculature a catheter having a balloon on a distal shaft section, the balloon has a flexural modulus of about 150,000 psi to about 300,000 psi and the balloon is formed from a substantially unblended copolymer of polybutylene terephthalate and polytetramethylene ether glycol terephthalate, the copolymer having a flexural modulus of greater than about 150,000 psi;
   b) positioning the catheter so that at least a length of the balloon is across a non-dilated region within the patient's vasculature; and
   c) expanding the balloon to simultaneously dilate the undilated lesion and implant the stent.

26. The method of claim 25 wherein the balloon has a compliance of less than about 0.045 mm/atm.

27. The method of claim 25 wherein the balloon has a compliance of less than about 0.02 mm/atm.

28. The method of claim 25 wherein the copolymer has a flexural modulus of at least about 175,000 psi.

* * * * *